(12) United States Patent
Kinoshiro et al.

(10) Patent No.: US 8,222,038 B2
(45) Date of Patent: Jul. 17, 2012

(54) METHOD FOR ANALYZING METAL SPECIMEN (75) Inventors: Satoshi Kinoshiro, Kanagawa (JP); Tomoharu Ishida, Chiba (JP)

(73) Assignee: JFE Steel Corporation (JP)

( * ) Notice: Subject to any disclaimer, the term of this patent is extended or adjusted under 35 U.S.C. 154(b) by 152 days.

(21) Appl. No.: 12/666,652

(22) PCT Filed: Jun. 26, 2008

(86) PCT No.: PCT/JP2008/062037
§ 371 (c)(1),
(2), (4) Date: Feb. 17, 2010

(87) PCT Pub. No.: WO2009/005112
PCT Pub. Date: Jan. 8, 2009

(65) Prior Publication Data
US 2010/0291692 A1 Nov. 18, 2010

(30) Foreign Application Priority Data

Jun. 29, 2007 (JP) ................................. 2007-171713
Jun. 23, 2008 (JP) ................................. 2008-162651

(51) Int. Cl.
*G01N 27/26* (2006.01)
*G01N 33/20* (2006.01)
(52) U.S. Cl. ............................ 436/73; 436/84; 205/790
(58) Field of Classification Search .................... 436/73, 436/78, 83, 84, 80
See application file for complete search history.

(56) References Cited

U.S. PATENT DOCUMENTS

2005/0241956 A1 11/2005 Saini
2010/0196189 A1* 8/2010 Nakagawa et al. ........... 420/114

FOREIGN PATENT DOCUMENTS

| JP | 59-058342 A | 4/1984 |
| JP | 62-284259 A | 12/1987 |
| JP | 08-122323 A | 5/1996 |
| JP | 2003-021646 A | 1/2003 |

OTHER PUBLICATIONS

"Handbook of Iron and Steel (Tekko Binran)," *The Iron and Steel Institute of Japan*, 4th edition (CD-ROM), vol. 4, section 2, 3.5 (original in Japanese) and 1 sheet (partial English translation).
Agne, *Saishin no Tekkou Joutai Bumseki*, 1979, pp. 40-53 (original in Japanese) and 1 sheet (English translation of Abstract).
"Methods for Atomic Absorption Spectrochemical Analysis of Iron and Steel," *JIS G 1257*, 1997, section 8.3.1.3, pp. 66-72 (original in Japanese) and 1 sheet (English translation of Abstract).

(Continued)

*Primary Examiner* — Robert J Hill, Jr.
*Assistant Examiner* — Dwan A Gerido
(74) *Attorney, Agent, or Firm* — DLA Piper LLP (US)

(57) ABSTRACT

A method for analyzing a metal specimen includes an electrolysis step of electrolyzing a metal specimen containing a reference element and a target element in an electrolytic solution, a sampling step of sampling a portion of the electrolytic solution, an analysis step of analyzing the sampled electrolytic solution, a concentration ratio-calculating step of calculating the concentration ratio of the target element to the reference element in the electrolytic solution on the basis of the analysis results, and a content-calculating step of calculating the content of the target element present in the form of a solid solution by multiplying the content of the reference element in the metal specimen by the obtained concentration ratio.

15 Claims, 3 Drawing Sheets

OTHER PUBLICATIONS

Ariga, Y. et al., "Development of Extracted Residue Analysis Method and Cu-Fe-P Alloy with Excellent Softening Resistance," *Materia Japan*, The Japan Institute of Metals, 2006, vol. 45, No. 1, p. 53 (original in Japanese) and 6 sheets (partial English translation).

"Isolation and Determination of Precipitates in High Alloys and Super Alloys (I)," *The Iron and Steel Institute of Japan "Tetsu-to-Hagane"*, 1993, vol. 79, No. 6, pp. 10-19 (original in Japanese) and 1 sheet (English translation of Abstract).

* cited by examiner

METHOD FOR ANALYZING METAL SPECIMEN

RELATED APPLICATIONS

This is a §371 of International Application No. PCT/JP2008/062037, with an international filing date of Jun. 26, 2008 (WO 2009/005112 A1, published Jan. 8, 2009), which is based on Japanese Patent Application Nos. 2007-171713, filed Jun. 29, 2007, and 2008-162651, filed Jun. 23, 2008, the subject matter of which is incorporated by reference.

TECHNICAL FIELD

This disclosure relates to methods for analyzing elements in metal specimens and particularly relates to methods for quickly and accurately determining the content of an element that is present in a metal specimen in the form of a solid solution.

BACKGROUND

Precipitates present in metal specimens significantly affect material properties such as fatigue properties, hot workability, cold workability, deep drawability, machinability, and electromagnetic properties depending on the shape, size, and distribution thereof.

To cite steel, techniques for enhancing properties of steel products by making use of fine precipitates have been remarkably improved in recent years. The development thereof has caused precipitates to be strictly controlled in production steps. The following contents vary gradually through production steps: the content of an added element present in a metal specimen in the form of a solid solution and the content of the added element present therein in the form of a precipitate. The content of an added element present in a metal specimen in the form of a solid solution is hereinafter referred to as solid solution content. The content of an element present in a metal specimen in the form of a precipitate is hereinafter referred to as precipitation content. For example, an added element combines with nitrogen or carbon during the solidification of molten steel and partly precipitates, whereby precipitates are formed. The precipitates are separated into solid solution fractions and precipitate fractions in a slab-heating step. Some of the solid solution fractions precipitate in a subsequent rolling step because of strain-induced precipitation and the rest of the solid solution fractions precipitates during subsequent transformation. Some of the solid solution fractions sometimes remain in products in the form of solid solutions depending on the cooling rate thereof.

As described above, to produce a good final product, it is necessary to control the change in amount of an added element present in the form of a precipitate or solid solution. For such control, it is essential to accurately analyze the solid solution content or precipitation content of the added element in steel.

Examples of precipitates and/or inclusions in steel materials include borides, phosphides, sulfides, nitrides, carbides, and oxides. Such precipitates and inclusions are hereinafter collectively referred to as precipitates.

Examples of known techniques for determining precipitates include an acid dissolution method, a halogen method, and an electrolytic method as disclosed in The Iron and Steel Institute of Japan, "Handbook of Iron and Steel, 4th edition (CD-ROM)," Vol. 4, Section 2, 3.5 or Agne, "Saishin no Tekkou Joutai Bunseki," p. 40, 1979. A similarity between the methods disclosed in The Iron and Steel Institute of Japan, "Handbook of Iron and Steel, 4th edition (CD-ROM)," Vol. 4, Section 2, 3.5 or Agne, "Saishin no Tekkou Joutai Bunseki," p. 40, 1979 is that a matrix is chemically dissolved in an extraction liquid and target precipitates are collected from the extraction liquid and then analyzed. The processes are selectively used depending on the type of the target precipitates. The acid dissolution and halogen methods cause the dissolution of carbides and sulfides and therefore are mostly used to selectively extract only oxide inclusions. An electrolytic method using a non-aqueous electrolytic solution is used to extract almost all inclusions from a steel material with no loss.

There is no known technique for directly analyzing the solid solution content of an added element. A similar technique is one disclosed in JIS G 1257 "Methods for atomic absorption spectrochemical analysis of Iron and Steel," 8.3.1.3, p. 70, 1997. JIS G 1257 "Methods for atomic absorption spectrochemical analysis of Iron and Steel," 8.3.1.3, p. 70, 1997 discloses a method for analyzing a filtrate obtained by the acid dissolution method, that is, a method for analyzing aluminum in acid-dissolved steel. In that method, the analysis result is the sum of the content of dissolved aluminum and the content of precipitated aluminum, which is acid-soluble, and therefore the solid solution content of aluminum cannot be accurately determined. Thus, to analyze a solid solution component only, an indirect method (hereinafter referred to as the indirect method) is probably used. In the indirect method, the precipitation content of a target component analyzed by the electrolytic method is subtracted from the content of the target component analyzed by, for example, a method for spark discharge atomic emission spectrometric analysis (JIS G 1253:2002) as given by the following equation:

$$[\text{sol. } A] = [\text{total } A] - [\text{pre. } A] \tag{1}$$

wherein [sol. A] represents the solid solution content of Element A, [total A] represents the content of Element A, and [pre. A] represents the precipitation content of Element A.

The precision of the analysis of each content in Equation (1) can be discussed using the standard deviation σ of the analysis result of the content. The standard deviation $\sigma_{sol.\,A}$ of the analysis result of the solid solution content [sol. A] is statistically given by the formula $(\sigma_{total\,A}^2 + \sigma_{pre.\,A}^2)^{1/2}$ from the standard deviation $\sigma_{total\,A}$ of the analysis result of the content [total A] and the standard deviation $\sigma_{pre.\,A}$ of the analysis result of the precipitation content [pre. A]. Therefore, when at least one of the standard deviation $\sigma_{total\,A}$ of the content and the standard deviation $\sigma_{pre.\,A}$ of the precipitation content is large, the analytical precision of the solid solution content [sol. A] determined by the indirect method is inevitably low. In general, the magnitude of error in an analysis result is proportional to the content of an element to be analyzed; hence, there is a problem in that the indirect method is low in analytical precision when the precipitation content is large.

Problems involved in analyzing fine precipitates in steel by the indirect method will now be described. Techniques for producing steel materials have been remarkably improved in recent years. Hence, the size of precipitates in steels has been reduced to several nanometers. In the case where fine precipitates are extracted from steel and then collected by filtration, the precipitation content has a negative error because some of the fine precipitates are unavoidably uncollected. In contrast, the solid solution content determined by the indirect method has a positive error. For a specimen containing fine precipitates, a filter with a pore size less than the size of precipitates to be analyzed is inevitably used. However, there is no filter capable of completely separating precipitate particles with a size of several nanometers from a liquid. If a filter having sub-nanometer-sized pores was developed, it is clear that a significant reduction in filtration rate causes a serious reduction in operability. These are not problems unique to steel. Japan Institute of Metals, "Materia Japan," Vol. 45, No. 1, p. 52, 2006 describes that a precipitate fraction of a target element cannot be separated from a solid solution fraction thereof in the case where fine precipitates are collected from a copper alloy by filtration. Therefore, it is probably difficult to apply the indirect method to a specimen containing fine precipitates.

There is no known technique capable of directly analyzing a precipitate component in a metal specimen probably because of the above problems.

Japanese Unexamined Patent Application Publication No. 59-58342 discloses a method for analyzing a solution by emission spectroscopy. In that method, the solution is prepared from a metal specimen and the content of each element is determined from the spectrum of the element, obtained by analyzing the solution, using a correction formula. The method disclosed in Japanese Unexamined Patent Application Publication No. 59-58342 is based on the following two assumptions:

(1) the sum of the contents of all elements contained in the metal specimen is equal to 100% by mass and
(2) there is a certain relationship between the spectrum intensity ratio of two elements measured at the same time and the content ratio of the two elements.

Since Assumptions (1) and (2) need to be simultaneously satisfied, almost all elements other than a target element in the solution need to be measured. Assumption (1) requires that the composition of the metal specimen needs to be substantially the same as the composition of the solution. Hence, that method cannot be used when the solution, which is prepared from the metal specimen, is different in composition from the metal specimen.

It could therefore be helpful to provide a method for readily, quickly, and directly determining the solid solution content of a target element in a metal specimen.

To achieve the object, a method for directly analyzing a solid solution component only has been investigated in such a manner that a matrix is dissolved in a non-aqueous electrolytic solution by an electrolytic method and the non-aqueous electrolytic solution is then analyzed.

For a specimen containing fine precipitates, there is the problem in that, even if a filtrate obtained by removing an undissolved residue from a non-aqueous electrolytic solution by filtration is used, the filtrate is contaminated with the fine precipitates and, therefore, the analysis result of the solid solution content has a positive error.

We thus provide:

[1] A method for analyzing a metal specimen comprises:
an electrolysis step of electrolyzing a metal specimen containing a reference element and a target element in an electrolytic solution;
a sampling step of sampling a portion of the electrolytic solution;
an analysis step of analyzing the sampled electrolytic solution;
a concentration ratio-calculating step of calculating the concentration ratio of the target element to the reference element in the electrolytic solution on the basis of the analysis results; and
a content-calculating step of calculating the content of the target element present in the form of a solid solution by multiplying the obtained concentration ratio by the content of the reference element in the metal specimen.

[2] In the metal specimen-analyzing method according to Item [1], the sampling step may include sampling a portion of the electrolytic solution during electrolysis.

[3] In the metal specimen-analyzing method according to item [1], the sampling step may include sampling a portion of the electrolytic solution after electrolysis.

[4] In the metal specimen-analyzing method according to Item [1], the sampling step may include removing the rest of the metal specimen from the electrolytic solution after electrolysis and then sampling a portion of the electrolytic solution.

[5] In the metal specimen-analyzing method according to Item [1], the sampling step may include filtering the electrolytic solution and then sampling a portion of the filtered electrolytic solution.

[6] In the metal specimen-analyzing method according to Item [1], the sampling step may include the electrolytic solution of 5 ml or less.

[7] In the metal specimen-analyzing method according to Item [1], the analysis step may include mixing the sampled electrolytic solution with an aqueous solution of a chelating agent to convert the reference element and the target element into water-soluble chelates, and then performing analysis.

[8] In the metal specimen-analyzing method according to Item [7], the chelating agent aqueous solution may be an aqueous solution of ethylenediaminetetraacetic acid.

[9] The metal specimen-analyzing method according to Item [1] may further include the step of dialyzing the sampled electrolytic solution through a semipermeable membrane to remove precipitates and inclusions.

[10] In the metal specimen-analyzing method according to Item [1], the analysis step may include:
an aqueous solution-preparing step of preparing an aqueous solution by adding a chelating agent to the sampled electrolytic solution;
a checking step of checking that the aqueous solution contains no fine particles; and
an aqueous solution-analyzing step of analyzing the checked aqueous solution.

[11] In the metal specimen-analyzing method according to Item [10], the checking step may include introducing the aqueous solution into a high-sensitivity analyzer and then checking the aqueous solution on the basis of the stability of the intensity of a signal obtained by time-resolved photometry.

[12] In the metal specimen-analyzing method according to Item [1], the reference element may be an element which forms no precipitate or inclusion.

[13] In the metal specimen-analyzing method according to Item [1], the metal specimen may be steel and the reference element may be iron.

[14] In the metal specimen-analyzing method according to Item [1], the metal specimen may be stainless steel and the reference element may be chromium or nickel.

[15] In the metal specimen-analyzing method according to Item [1], the metal specimen may be a copper alloy and the reference element may be copper.

Our methods are capable of accurately and directly determining the solid solution content of a target element in a metal specimen. The method is applicable to a metal specimen containing nanometer- or sub-nanometer-sized fine precipitates, is insensitive to the size and amount of precipitates, and is applicable to any metal specimens.

A portion of an electrolytic solution is sampled and then analyzed and the concentration ratio of a target element to a reference element in the electrolytic solution is used to determine the solid solution content of the target element. Hence, the solid solution content of the target element can be readily and quickly determined. Furthermore, the following problems are solved: environmental problems caused by the use of non-aqueous electrolytic solutions and problems involved in quantitative reproducibility due to the volatility thereof.

The solid solution content of an element in a metal specimen is an important evaluation factor for promoting the development of metal products or an important factor for assuring product quality. Therefore, our methods are industrially advantageous because the solid solution content of a target element in a metal specimen can be directly and accurately determined.

SUMMARY

We investigated specimens containing fine precipitates by an electrolytic method using a non-aqueous electrolytic solution and obtained the results below:

(A) In the case of sampling an electrolytic solution during or after the electrolysis of a metal specimen in such a state that precipitates are attached to the metal specimen, all the precipitates are attached to the rest (surface) of the metal specimen that remains during or after the electrolysis thereof.

(B) The electrolytic solution contains a target element extracted only from solid solutions.

(C) The solid solution content of the target element can be determined by analyzing the electrolytic solution without being affected by the precipitates.

We investigated methods for analyzing target elements in non-aqueous electrolytic solutions on the basis of the above results. There are probably problems below in accurately determining a metal element in a non-aqueous solvent:

(a) In the case of directly analyzing an electrolytic solution or analyzing the electrolytic solution diluted with another organic solvent, organic solvents used are difficult to handle because it is difficult to keep the volume of the organic solvents constant because of the volatility thereof and safety measures need to be taken against fire, harmful effects on the human body, and so on.

(b) Organic solvents that can be directly analyzed with element analyzers are limited and most of non-aqueous electrolytic solutions are inappropriate for the element analyzers.

(c) Results obtained by an electrolytic method in which a solution is prepared from a solid and then analyzed are expressed in mass per unit volume (for example, g/l). Hence, the mass of a dissolved target element and the mass of the dissolved solid need to be calculated to determine the content of the target element in the solid on a mass basis. To determine the loss of the target element, the volume of a liquid containing the target element needs to be accurately measured. However, it is difficult to accurately measure the volume of a non-aqueous electrolytic solution and, therefore, analysis results thereby obtained are problematic in accuracy.

(d) In the case of analyzing an aqueous solution prepared from a dried electrolytic solution, a large amount of the electrolytic solution needs to be dried (for example, several hundred milliliters of an electrolytic solution is used to electrolyze a steel material). This is complicated because a chelating agent that is a component of the electrolytic solution and a metal component dissolved in the electrolytic solution are concentrated and therefore the evaporation rate of the electrolytic solution becomes low late in the course of evaporation.

Even if a target element in an electrolytic solution could be analyzed, there remains the problem that the target element is readily and quickly analyzed.

We investigated whether this problem could be solved in such a manner that the whole of the electrolytic solution is not analyzed, but a portion of the electrolytic solution is sampled and then analyzed. As a result, we found that the solid solution content of a target element can be determined from the concentration of the target element in a liquid in such a manner that the solid solution concentration of the target element is relatively determined using an element insensitive to the phase transition from solid to liquid as a reference, that is, using a reference element. That is, it has been appreciated that the solid solution content of the target element can be determined without using a large amount of an organic solvent in such a manner that the ratio of the concentration of the target element to the concentration of the reference element in the sampled electrolytic solution is corrected with the content of the reference element in a solid specimen, the content of the reference element being determined by another method.

From the above investigation, it is clear that the solid solution content sol. $C_i$ of a target element i in a metal specimen (solid) can be determined in such a manner that the concentration $K_i$ of the target element i and the concentration $K_m$ of a reference element m in a sampled electrolytic solution are determined and the ratio $K_i/K_m$ is multiplied by the content $C_m$ of the reference element in the metal specimen (solid) (see Equation (2) below). The use of this concept allows the solid solution content of the target element to be determined without analyzing the whole of the electrolytic solution.

$$sol \cdot C_i = \frac{K_i}{K_m} \times C_m \qquad (2)$$

Our methods are characterized in that a metal specimen is electrolyzed in an electrolytic solution, a portion of the electrolytic solution is sampled during electrolysis and/or after electrolysis, the sampled electrolytic solution is analyzed, and the solid solution content of a target element is determined from the analysis results by Techniques (1) and (2) below. The target element and a reference element are selected from elements contained in the metal specimen.

(1) The ratio of the concentration of the target element to the concentration of the reference element in the sampled electrolytic solution is calculated.

(2) The concentration ratio calculated by Technique (1) is multiplied by the content of the reference element in the metal specimen.

The basic technical concept is as described below:
1) The target element contained only in solid solutions is extracted into the electrolytic solution in such a manner that the electrolytic solution is sampled during or after electrolysis in such a state that precipitates are attached to the metal specimen.
2) A portion of the electrolytic solution is sampled.
3) The concentration ratio of the target element to the reference element in the sampled electrolytic solution is corrected with the content of the reference element in a solid, the content of the reference element being determined by another technique.

For example, an element contained in the metal specimen is separated into a portion that forms solid solutions in a matrix and a portion that reacts with nitrogen, oxygen, or another element to form precipitates. In particular, in the case of electrolyzing a steel specimen in a non-aqueous electrolytic solution containing a chelating agent, a support electrolyte, and an organic solvent, a solid solution portion and a reference element are dissolved in the electrolytic solution and a precipitate portion is exposed on the surface of the specimen in the form of an undissolved residue. Since exposed precipitates are supposed to be attached to the steel specimen, which is an anode, by electrostatic attraction, the precipitates can be taken out of the electrolytic solution together with the specimen. Hence, the solid solution portion and the precipitate portion can be readily separated from each other.

The content of a solid solution portion can be determined by measuring the amount of a target element dissolved in a separated electrolytic solution. However, a non-aqueous electrolytic solution contains an organic solvent, such as methanol, having high volatility and the volume thereof is several milliliters. Hence, it is difficult to measure the content of an inorganic element. Therefore, the content of a target element in a solid solution portion in steel is determined as described below;
   (1) An appropriate amount of a sample is taken from several milliliters of an electrolytic solution and then dried.
   (2) An aqueous solution is prepared by dissolving the dried sample in a mineral acid such as nitric acid and the target element and a reference element are analyzed by an appropriate solution analysis technique.
   (3) The content of the target element in the solid solution portion in steel is determined in such a manner that the concentration ratio of the target element to the reference element is multiplied by the concentration of the reference element in a solid.

Unlike Japanese Unexamined Patent Application Publication No. 59-58342, our methods are therefore effective in analyzing at least one target element and at least one reference element and is applicable to the case where a solution sample is different in composition from a metal specimen because the solution sample contains a solid solution component and a host phase only other than precipitates.

Our methods will now be described in detail.
1) A Metal Specimen is Electrolyzed in an Electrolytic Solution.

An element dissolved in the electrolytic solution and a chelating agent contained in the electrolytic solution form a complex. Hence, a substance obtained by the evaporation of methanol has an advantage that the substance can be readily converted into an aqueous solution. Therefore, examples of a chelating agent contained in a non-aqueous electrolytic solution include acetylacetone, maleic anhydride, triethanolamine, methyl salicylate, and salicylic acid. A support electrolyte used is preferably tetramethylammonium chloride, lithium chloride, or the like.

Conditions for electrolysis are not particularly limited and are appropriately designed depending on the ability of the chelating agent to form a complex with a target element, the stability of precipitates containing the target element, and/or the like.

2) A Portion of the Electrolytic Solution is Sampled During Electrolysis and/or after Electrolysis.

The electrolytic solution portion may be sampled in such a state that the precipitates are attached to the metal specimen. The time to sample the electrolytic solution portion is determined depending on a material, a condition, and/or the like. However, the electrolytic solution portion is preferably sampled during electrolyzing because of the electrostatic attraction of the precipitates to the metal specimen.

In the case of sampling the electrolytic solution after the termination of electrolyzing, the rest of the metal specimen may be immersed in the electrolytic solution. Since the concentration of a dissolved metal in the upper layer of the electrolytic solution is usually low, it is preferred that a lower layer of the electrolytic solution be sampled or the electrolytic solution be sampled after the rest of the metal specimen is removed from the electrolytic solution and the resulting electrolytic solution is stirred.

If it is concerned that the precipitates are distributed in the electrolytic solution, the sampled electrolytic solution may be analyzed after the sampled electrolytic solution is filtered through an appropriate filter or is centrifuged such that the precipitates are removed from the sampled electrolytic solution. Alternatively, after the electrolytic solution is filtered through an appropriate filter or is centrifuged such that the precipitates are removed from the electrolytic solution, a sample taken from the filtered electrolytic solution may be analyzed.

The amount of the sampled electrolytic solution is not particularly limited and may be sufficient for analysis in view of the sensitivity of an analyzer used in a subsequent step of analyzing the electrolytic solution. In particular, the amount of the sampled electrolytic solution is preferably 5 ml or less and more preferably 1 ml or less because 1 ml of the electrolytic solution is dried up in about five minutes.

3) The Sampled Electrolytic Solution is Analyzed.

A technique for analyzing the sampled electrolytic solution is not particularly limited and is preferably inductively coupled plasma (ICP) emission spectrometry, ICP mass spectrometry, or atomic absorption spectroscopy.

In the case of analyzing the sampled electrolytic solution by the element analysis, it is preferred that a non-aqueous solvent be removed from the sampled electrolytic solution by drying and the resulting electrolytic solution is formed into an aqueous solution.

Some target elements form precipitates when the electrolytic solution, which contains the non-aqueous solvent, is converted into the aqueous solution. This causes various problems during the analysis of elements. Therefore, these target elements can be analyzed with no problem in such a manner that non-aqueous solvent-soluble complexes of these target elements are converted into water-soluble complexes when the electrolytic solution is converted into the aqueous solution. That is, the problem that such precipitates are formed when the electrolytic solution is converted into the aqueous solution can be solved in such a manner that an aqueous solution of a chelating agent is added to and mixed with the sampled electrolytic solution, the target and reference elements in the sampled electrolytic solution are thereby converted into complexes in the form of water-soluble chelates, and these complexes are analyzed. This enables rapid, accurate concentration measurement. The chelating agent is preferably a salt of ethylenediaminetetraacetic acid (hereinafter simply referred to as EDTA), which has high affinity to metal elements. Examples of the chelating agent include, but are not limited to, 1,2-cyclohexanediaminetetraacetic acid (CyDTA), 1,2-dihydroxy-3,5-benzenedisulfonic acid, and a disodium salt (Tiron).

In the case where most of the specimen is electrolyzed or the specimen contains a large amount of the precipitates, some of the precipitates are separated from the specimen and are dispersed in the electrolytic solution. This may cause a positive error in the analysis data of a solid solution. In this case, the precipitates can be removed from the electrolytic solution in such a manner that the electrolytic solution is dialyzed through a semipermeable membrane.

When it is known that the precipitates, which are dispersed in the electrolytic solution, have a large size greater than or equal to several hundred nanometers, the following filtrate may be analyzed: a filtrate obtained by filtering the electrolytic solution through a filter having a pore size less than the size of the precipitates. A solution containing the water-soluble chelates may be dialyzed and then analyzed as required. Metal complexes contained in the solution containing the water-soluble chelates migrate into a dialysate (pure water) through a semipermeable membrane. However, the precipitates, which are particles, cannot migrate thereinto. This treatment is effective when the precipitates are contained in the sampled electrolytic solution.

Since it takes a long time to perform dialysis using a semipermeable membrane, the application of such dialysis to all cases is inadvisable. It is difficult to determine whether the electrolytic solution lacks the precipitates from the composition or size of the specimen. Hence, the necessity of dialysis is preferably determined by a simple technique. In the method, analysis for determining the solid solution content is intended for aqueous solution samples. The method is readily applicable to various analyzers.

Figure 1:
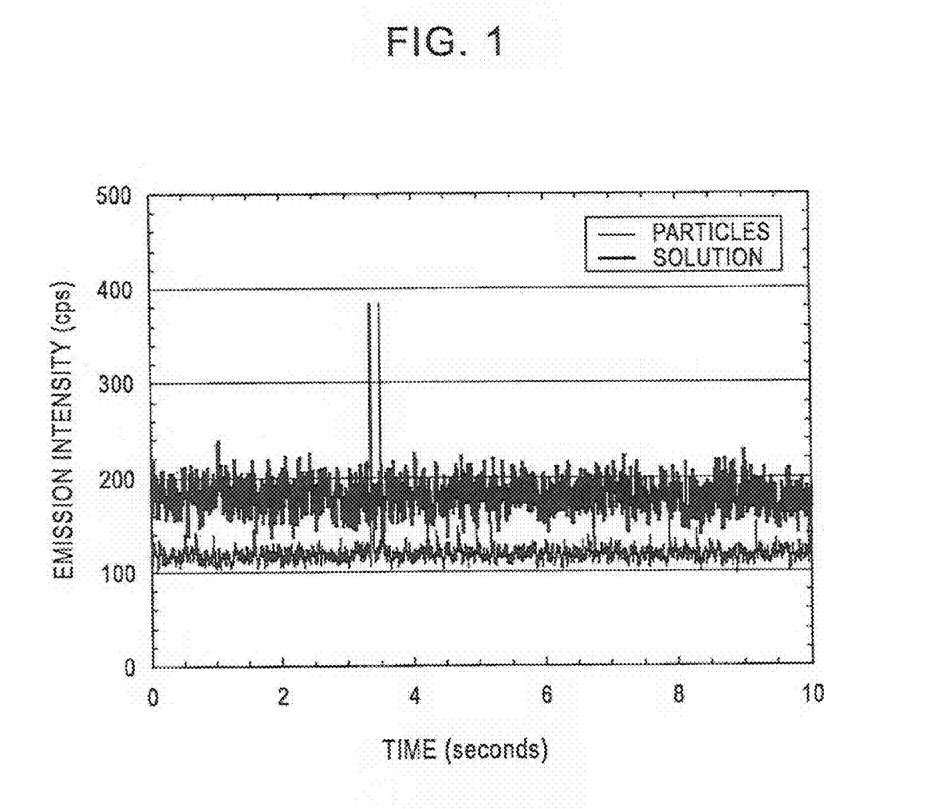
FIG. 1 is a graph showing the change in emission intensity of a liquid containing particles and that of a liquid containing no particles as determined by ICP-AES.

Possible techniques to which the method is applicable are high-sensitive analysis techniques such as ICP-AES and ICP-MS. Analyzers for these techniques mostly have a time-resolved photometric function for the purpose of sensitivity adjustment. If the analyzers do not have such a function, voltage analogue signals corresponding to emission intensities measured with detectors can be relatively readily taken out of the analyzers. This has led to a finding that the contamination of fine particles can be determined by a procedure below. That is, it has been appreciated that the presence of fine particles can be checked in such a manner that an aqueous solution containing a chelating agent is directly introduced into an analyzer and the time-resolved emission intensity thereof is measured. FIG. 1 shows the change in emission intensity of a liquid containing particles and that of a liquid containing no particles as determined by ICP-AES. A dissolved component is detected from the liquid containing no particles and the detected emission intensity thereof is stable. Intermittent strong peaks are detected from the liquid containing the particles although the particles have a fine size of several ten nanometers or less. This is because a large number of elements to be measured are excited in a short time by the presence of the particles and therefore are detected. This can cause a positive error in view of the determination of a solid solution component.

Figure 2:
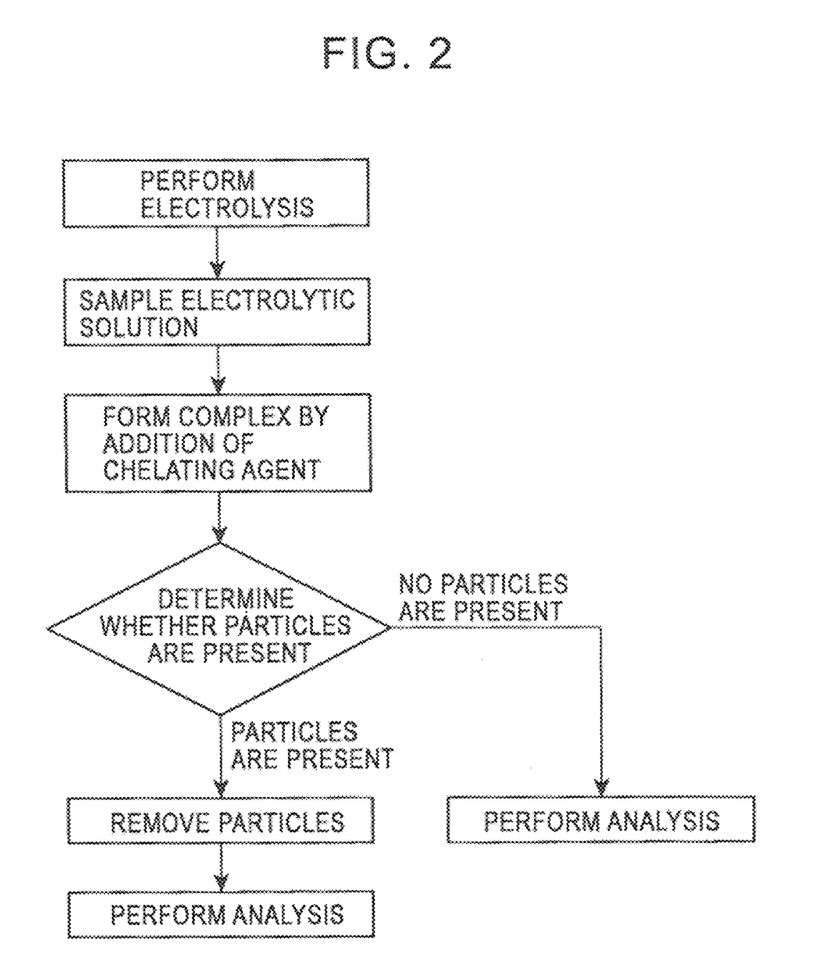
FIG. 2 is an exemplary flowchart including a determination step.

The use of this technique enables the determination of whether accurate size classification such as dialysis is performed. FIG. 2 shows an exemplary flowchart including such a determination step. Analysis for determination may use another technique. When the detection frequency of peaks indicating the presence of the particles is negligibly small with respect to analysis data, dialysis need not be performed even if such peaks are detected. Details of specific determination standards are preferably fixed depending on samples or cases.

The relative concentration of the target element and that of the reference element in the sampled electrolytic solution are important factors as described above. Therefore, the amount of the sampled electrolytic solution need not be accurately weighed or it is not problematic at all that a portion of the sampled electrolytic solution is lost during drying or dissolution.

The reference element is preferably iron in the case of analyzing steel; iron, chromium, or nickel in the case of analyzing stainless steel; or copper in the case of analyzing a copper alloy. The following element is preferably selected as the reference element: an element which is a principal component of the metal specimen and which forms no precipitates or forms a slight amount of precipitates. Examples of the reference element are not limited to those described above. Any element contained in the metal specimen to a certain extent can be used as the reference element. A plurality of elements may be selected as reference elements. For example, two or more of iron, chromium, and nickel may be selected in the case of analyzing stainless steel. The concentration of the reference element in the electrolytic solution may be the sum of the concentrations of the selected elements in the electrolytic solution and the content of the reference element may be the sum of the contents of the selected elements.

4) The solid solution content of the target element is determined by Techniques (1) and (2) below on the basis of the analysis results obtained in Item 3).

(1) The concentration $K_i$ of the target element i and the concentration $K_m$ of the reference element m in the electrolytic solution are determined and the concentration ratio ($K_i/K_m$) is then calculated.

(2) The concentration ratio calculated by Technique (1) is multiplied by the content of the reference element $C_m$ in the metal specimen.

Results obtained by Techniques (1) and (2) allow the solid solution content sol. $C_i$ of the target element i in a solid to be determined (see Equation (2) below):

$$sol \cdot C_i = \frac{K_i}{K_m} \times C_m. \tag{2}$$

A suitable technique for determining the content of the reference element in the solid is that the sum of the contents of elements other than the reference element is subtracted from 100%, the contents thereof being determined by a method for spark discharge atomic emission spectrometric analysis (JIS G 1253:2002), a method for X-ray fluorescence spectrometric analysis (JIS G 1259:1997), ICP emission spectrometry, or ICP mass spectrometry.

EXAMPLE 1

Analyses of the solid solution content sol. $C_V$ of vanadium (V) and the solid solution content sol. $C_{Nb}$ of in steel specimens are described below in detail.

Japanese iron and steel certified reference materials shown in Table 1 were cut into specimens with an appropriate size. The specimens were sufficiently surface-ground and then analyzed by an inventive method and comparative method described below. The composition values of elements other than iron shown in Table 1 are certified values. The composition value of iron is a calculated value determined by subtracting the sum of the composition values of the elements other than iron from 100%.

TABLE 1

| Components | C | Si | Mo | V | Ti | Nb | Others | mass percent (Fe) |
|---|---|---|---|---|---|---|---|---|
| JSS165-4 | 0.051 | (0.01) | 0.015 | 0.30 | 0.015 | 0.21 | 0.374 | (99.04) |
| JSS1007-1 | 0.0024 | 0.006 | 0.030 | 0.030 | 0.021 | 0.030 | 0.22 | (99.66) |
| JSS1008-1 | 0.0032 | 0.009 | 0.062 | 0.060 | 0.052 | 0.060 | 0.44 | (99.32) |

Inventive Method

About 0.5 g of each specimen was electrolyzed at a constant potential in about 300 ml of a 10% AA electrolytic solution (ten volume percent acetylacetone, one mass percent tetramethylammonium chloride, and methanol).

Just before energization was terminated, about 1 ml of a sample was taken from about 300 ml of the electrolytic solution while the specimen was kept in the electrolytic solution. The sample was dried in a beaker. The residue thereby obtained was dissolved in nitric acid by heating, whereby an analytical solution was prepared (none of the rest of the electrolytic solution and residual materials attached to the specimen was subjected to analyses below).

The concentration ($K_v$) of vanadium, the concentration ($K_{Nb}$) of niobium, and the concentration ($K_{Fe}$) of iron, which was selected as a reference element, in the analytical solution were each determined with an ICP mass spectrometer. The concentration ratios ($K_v/K_{Fe}$ and $K_{Nb}/K_{Fe}$) were multiplied by the content ($C_{Fe}$) of the reference element (Fe) (the composition value of iron in Table 1), whereby the solid solution content (sol. $C_v$) of vanadium and the solid solution content (sol. $C_{Nb}$) of niobium in the specimen were determined.

Comparative Method

Since there was no conventional technique for directly determining the solid solution content of a metal element in a steel specimen, a comparative method used was a precipitate analysis method recommended by The Iron and Steel Institute of Japan. Precipitates in the Japanese iron and steel certified reference materials were analyzed by the comparative method, whereby the precipitation content of each target element. The solid solution content of the target element was determined by subtracting the precipitation content thereof from a certified value (the composition of steel).

About 0.5 g of each specimen was electrolyzed at a constant potential in about 300 ml of a 10% AA electrolytic solution. After electrolyzing was terminated, the specimen was gently taken out of the electrolytic solution and then transferred to a beaker containing about 100 ml of methanol. Precipitates attached to the specimen were removed by applying ultrasonic vibration to the beaker. After the specimen exhibited a metallic luster, ultrasonic vibration was stopped and the specimen was taken out of the beaker. The specimen was cleaned with methanol and then dried. After being dried, the resulting specimen was measured for weight with a balance. The weight loss of the specimen by electrolysis was determined by subtracting the weight of the electrolyzed specimen from the weight of the unelectrolyzed specimen.

The electrolytic solution and the methanol used were suction-filtered through a filter with a pore size of 0.2 µm, whereby a residue was collected on the filter. The residue and the filter were dissolved in an acid mixture by heating, whereby a solution was prepared. This solution was analyzed with an ICP emission spectrometer, whereby the absolute amount of vanadium and the absolute amount of niobium in the residue were determined. The precipitation content of vanadium and the precipitation content of niobium were determined by dividing the absolute amount of vanadium and the absolute amount of niobium, respectively, in the residue by the weight loss of the specimen. Results obtained as described above are summarized in Table 2.

TABLE 2

| | Solid solution content (mass percent) | | | |
|---|---|---|---|---|
| | V | | Nb | |
| | Inventive method | Comparative method | Inventive method | Comparative method |
| JSS165-4 | 0.224 | 0.224 | 0.000 | 0.000 |
| JSS1007-1 | 0.030 | 0.029 | 0.014 | 0.015 |
| JSS1008-1 | 0.059 | 0.059 | 0.047 | 0.046 |

Table 2 shows that the inventive method agrees in solid solution content with the comparative method. This supports that the solid solution content determined by the inventive method and the solid solution content determined by the comparative method are both correct. In Example 1, the Japanese iron and steel certified reference materials containing sufficiently large precipitates were used to verify the inventive method and therefore the comparative method was effective in accurately determining the solid solution concentration of a metal. However, the comparative method is ineffective in accurately determining the solid solution concentration of a metal in a specimen containing nanometer- or sub-nanometer-sized precipitates. The inventive method is the sole method for accurately determining the solid solution content of a metal in a specimen containing nanometer- or sub-nanometer-sized precipitates at present.

Table 3 shows the time taken to analyze a single specimen by each of the inventive method and the comparative method. The time taken for electrolysis, which is common to the methods, is excluded.

TABLE 3

| | Inventive method | | Comparative method | |
|---|---|---|---|---|
| Operations (minutes) | Sampling | 1 | Distribution in methanol | 5 |
| | Drying | 5 | Filtration | 15 |
| | Dissolution by heating | 5 | Residue decomposition | 15 |
| | Measurement | 10 | Cooling and volume determination | 30 |
| | | | Measurement | 10 |
| Total (minutes) | | 21 | | 75 |

Table 3 shows that the inventive method is shorter in analysis time, simpler, and more rapid than the comparative method because the inventive method lacks complicated steps such as filtration step and residue decomposition and time-consuming steps such as cooling and volume determination.

EXAMPLE 2

Analyses of the solid solution content sol. $C_{Ti}$ of titanium in each steel specimen used in Example 2 are described below in detail.

Two steel ingots having the composition shown in Table 4 were prepared, heated at 1250° C. for 60 minutes, rolled into sheets at a finishing temperature of 1050° C. The sheets were heat-treated under conditions shown in Table 5. After being cooled, the sheets were cut into specimens with an appropriate size. After being sufficiently surface-ground, the specimens were each analyzed by the inventive or comparative method.

The composition values of elements other than iron shown in Table 4 are values obtained by a common method such as a method for spark discharge atomic emission spectrometric analysis. The composition value of iron is a calculated value determined by subtracting the sum of the composition values of the elements other than iron from 100%.

The specimens were analyzed for dissolved titanium by the inventive or comparative method four times.

TABLE 4

| C | Mn | Ti | N | Others | mass percent (Fe) |
|---|----|----|----|--------|-------------------|
| 0.05 | 1.80 | 0.201 | 0.0039 | 0.15 | 97.80 |

TABLE 5

| | Heating conditions | | Outlines of precipitates |
|---|---|---|---|
| Specimens | Temperature (° C.) | Time (minutes) | observed with an electronic microscope. |
| Specimens A | 450 | 60 | Precipitates with a size of 1 μm or more. |
| Specimens B | 550 | 60 | Precipitates with a size of 1 μm or more and precipitates with a size of about 2 nm. |

The schematic size of precipitates, contained in the specimens, observed with an electronic microscope is shown in Table 5. Table 5 shows that Specimens A contain precipitates with an ordinary size and Specimens B contains nanometer-sized fine precipitates.

Inventive Method

About 0.5 g of each specimen was electrolyzed at a constant potential in about 300 ml of a 10% AA electrolytic solution (ten volume percent acetylacetone, one mass percent tetramethylammonium chloride, and methanol). Just before energization was terminated, about 1 ml of a sample was taken from about 300 ml of the electrolytic solution while the specimen was kept in the electrolytic solution. The sample was dried in a beaker. The residue thereby obtained was dissolved in nitric acid by heating, whereby an analytical solution was prepared (none of the rest of the electrolytic solution or residual materials attached to the specimen was subjected to analyses below).

The concentration ($K_{Ti}$) of titanium and the concentration ($K_{Fe}$) of iron, which was selected as a reference element, in the analytical solution were each determined with an ICP mass spectrometer. The concentration ratio ($K_{Ti}/K_{Fe}$) was multiplied by the content ($C_{Fe}$) of the reference element (the composition value of iron in Table 4), whereby the solid solution content (sol. $C_{Ti}$) of titanium in the specimen was determined.

Comparative Method

Since there was no conventional technique for directly determining the solid solution content of a metal element in a steel specimen, a comparative method used was a precipitate analysis method recommended by The Iron and Steel Institute of Japan. The precipitation content of titanium in each specimen was determined by the comparative method. The solid solution content of titanium was determined by subtracting the precipitation content thereof from the content of titanium in the steel shown in Table 4.

About 0.5 g of the specimen, which was weighed with a balance in advance, was anodically electrolyzed at a constant potential in about 300 ml of a 10% AA electrolytic solution.

After energization was terminated, the specimen was gently taken out of the electrolytic solution and then transferred to a container containing about 100 ml of methanol. Precipitates attached to the specimen were removed by applying ultrasonic vibration to the container. After the specimen exhibited a metallic luster, ultrasonic vibration was stopped and the specimen was taken out of the container. The specimen was cleaned with methanol and then dried. After being dried, the resulting specimen was measured for weight with a balance. The weight loss of the specimen by electrolysis was determined by subtracting the weight of the electrolyzed specimen from the weight of the unelectrolyzed specimen.

The electrolytic solution and the methanol used were suction-filtered through a filter with a pore size of 0.2 μm, whereby a residue was collected on the filter. The residue and the filter were dissolved in a mixture of nitric acid, perchloric acid, and sulfuric acid by heating, whereby a solution was prepared. This solution was analyzed with an ICP emission spectrometer, whereby the absolute amount of titanium in the residue was determined. The precipitation content of titanium was determined by dividing the absolute amount of titanium in the residue by the weight loss of the specimen. The solid solution content of titanium was calculated by subtracting the precipitation content of titanium from the composition value of titanium in Table 4.

Results obtained by the inventive and comparative methods as described above are summarized in Table 6.

TABLE 6

| | Inventive method | | | Comparative method | | |
|---|---|---|---|---|---|---|
| | Solid solution Content (mass ppm) | | Standard deviation | Solid solution content (mass ppm) | | Standard deviation |
| Specimens | Measurements | Averages | σ (mass ppm) | Measurements | Averages | σ (mass ppm) |
| Specimens A | 1505 | 1537 | 30 | 1518 | 1542 | 24 |
| | 1520 | | | 1528 | | |
| | 1573 | | | 1572 | | |
| | 1550 | | | 1549 | | |

TABLE 6-continued

| | Inventive method | | | Comparative method | | |
|---|---|---|---|---|---|---|
| | Solid solution Content (mass ppm) | | Standard deviation | Solid solution content (mass ppm) | | Standard deviation |
| Specimens | Measurements | Averages | σ (mass ppm) | Measurements | Averages | σ (mass ppm) |
| Specimens B | 850<br>865<br>796<br>800 | 827 | 35 | 1421<br>1269<br>1408<br>1346 | 1361 | 70 |

The accuracy of the inventive method is compared with that of the comparative method from Table 6. For Specimens A, which contain precipitates with a normal size on the order of micrometers, the average of measurements (solid solution content) determined by the inventive method substantially agrees with that by the comparative method. This shows that the result obtained by the inventive method is the correct solid solution content of titanium excluding precipitates. For Specimens B, which contain fine precipitates, the solid solution content determined by the inventive method is extremely less than that by the comparative method. This is because the precipitates contained in Specimens B are very fine in size and small in amount, some of the precipitates are not collected by filtration, the precipitation content of titanium is small, and therefore the solid solution content of titanium determined by the comparative method is computationally large. This proves that the accuracy of the solid solution content determined by the inventive method is higher than that by the comparative method in the case of analyzing a specimen containing precipitates that are fine in size and small in amount.

The analytical precision of the inventive method is compared with that of the comparative method below. For Specimens A, the standard deviation σ of the comparative method is slightly less than that of the inventive method. For Specimens B, the standard deviation σ of the inventive method is, however, extremely less than that of the comparative method.

For Specimens A, 20 percent or more of the titanium contained therein is present in precipitates and 80 percent or less thereof is present in solid solutions. Although the inventive method is intended for the analysis of the solid solutions, in which 80 percent or less of the titanium contained is present, the comparative method is intended for the analysis of the precipitates, in which 20 percent or more of the titanium contained is present. This is probably the reason for that the standard deviation σ of the comparative method is small.

For Specimens B, the amount of precipitated titanium (precipitates) is about 60 percent of the content of titanium therein. Therefore, the inventive method, which is intended for the analysis of solid solutions in which about 40 percent of the titanium contained is present, is superior in precision to the comparative method, which is intended for the analysis of precipitates in which about 60 percent of the titanium contained is present. In the comparative method, the collection of the precipitates by filtration is unstable because of the size and amount of the precipitates. This is probably the reason for that the analytical precision of the comparative method is low. Therefore, the inventive method is more effective in accurately analyzing a specimen containing fine precipitates, particularly an element with a high precipitation rate, as compared to the comparative method.

As described above, it is clear that the inventive method is capable of directly analyzing the solid solution content of a target element in a specimen with high accuracy without being affected by the fineness and/or amount of precipitates contained in the specimen.

EXAMPLE 3

Analyses of samples taken from electrolytic solutions used to electrolyze steel specimens in Example 3 are described below in detail.

About 0.5 g of a Japanese iron and steel certified reference material, JSS1008-1, shown in Table 1 was anodically electrolyzed at a constant potential in about 300 ml of a 10% AA electrolytic solution. About 1 ml of samples were taken from the used electrolytic solution and then each treated by an inventive method or comparative method below, whereby the methods were compared.

Inventive Method

About 1 ml of a sample was taken from about 300 ml of the electrolytic solution, placed into a test tube, and then mixed with 0.4 ml of a 0.1 mol/L aqueous solution of diammonium ethylenediaminetetraacetate. The mixture was dried. The residue thereby obtained was dissolved in about 20 ml of pure water by heating, whereby an analytical solution was prepared. The analytical solution was introduced into an ICP mass spectrometer, whereby the ion intensity of each of vanadium, iron, and molybdenum was measured with time.

Comparative Method

About 1 ml of a sample was taken from about 300 ml of the electrolytic solution, placed into a test tube, and then dried. The residue thereby obtained was dissolved in 2 ml of (1+1) nitric acid by heating. The nitric solution was diluted with pure water to a volume of about 20 ml, whereby an analytical solution was prepared. The analytical solution was introduced into an ICP mass spectrometer, whereby the ion intensity of each of vanadium, iron, and molybdenum was measured with time.

Figure 3:
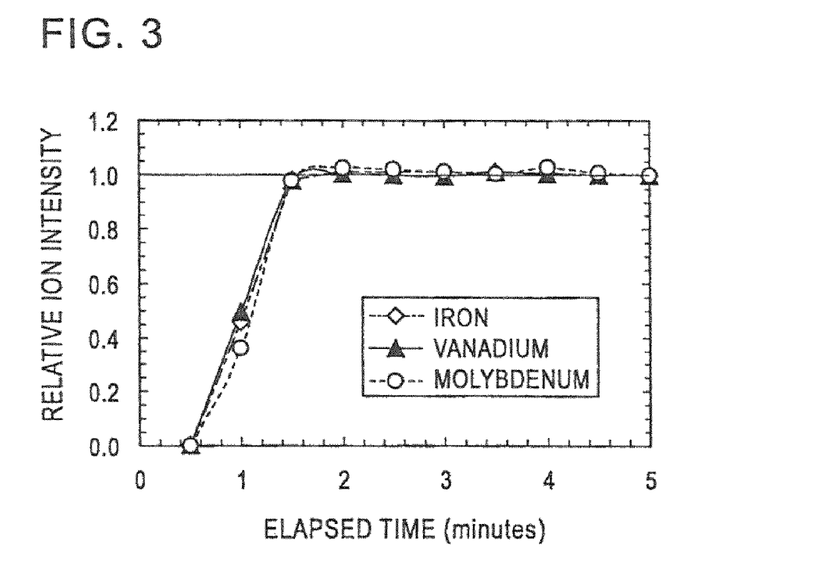
FIG. 3 is a graph showing the time-dependent change in ion intensity.
Figure 4:
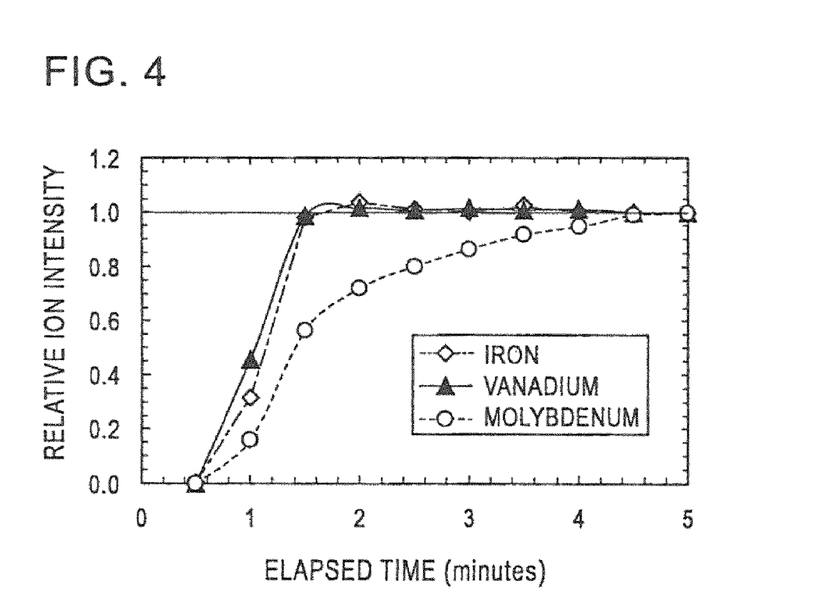
FIG. 4 is a graph showing the time-dependent change in ion intensity measured by a comparative method.

FIGS. 3 and 4 show the time-dependent change in ion intensity measured by the inventive method and that by the comparative method, respectively, with a value obtained after five minutes from the start of monitoring being used as a reference. In the inventive method, the ion intensity of each of vanadium, iron, and molybdenum reaches a constant value after about two minutes from the start of monitoring. In the comparative method, the ion intensity of each of vanadium and iron reaches a constant value after about two minutes from the start of monitoring. However, the ion intensity of molybdenum is still unstable after five minutes from the start of monitoring.

In general, a liquid sample is analyzed with an ICP mass spectrometer in such a manner that the liquid sample is drawn into a capillary tube and is subjected to atomization, ionization, and then detection. In the case of starting monitoring at the point of time when the liquid sample is introduced into the spectrometer, it takes a certain time to detect an element in the liquid sample. In usual, this time rarely depends on elements. The behavior of molybdenum measured by the comparative method is due to that a portion of molybdenum in the sampled electrolytic solution becomes unstable to form fine precipitates in the nitric solution and therefore molybdenum takes a longer time to reaches a detector of the spectrometer as compared to vanadium and iron, which are completely dissolved in the nitric solution. In the inventive method, ions of molybdenum in the analytical solution react with EDTA to form stable water-soluble chelates and therefore molybdenum is prevented from forming precipitates. Hence, the ion intensity of molybdenum probably behaves as well as that of vanadium and iron.

To achieve an accurate analytical measurement, analysis needs to be performed after the stabilization of ion intensity. It is clear that the comparative method, therefore, requires a long analysis time.

EXAMPLE 4

Analyses of dissolved titanium in steel materials in the case of dispersing precipitates in electrolytic solutions using Specimens B shown in Table 5 in Example 4 are described below in detail. Dissolved titanium was analyzed by an inventive method or a comparative method four times.

Inventive Method

Specimens B shown in Table 5 were used as samples. About 0.5 g of each specimen was electrolyzed at a constant potential in about 300 ml of a 10% AA electrolytic solution (ten volume percent acetylacetone, one mass percent tetramethylammonium chloride, and methanol). After electrolysis was finished, ultrasonic waves were applied to the specimen in the electrolytic solution, whereby precipitates attached to the specimen were intentionally dispersed in the electrolytic solution. About 5 ml of the electrolytic solution was sampled into a beaker while being stirred and then mixed with 2 ml of a 0.1 mol/L aqueous solution of diammonium ethylenediaminetetraacetate. The mixture was dried. The residue thereby obtained was dissolved in about 50 ml of pure water by heating, whereby a solution was prepared. This solution was contacted with a dialysate (pure water) for 12 hours or more with a semipermeable membrane (a molecular-weight cutoff of 2000) placed therebetween and the dialysate was then recovered. The recovered dialysate was mixed with nitric acid, perchloric acid, and sulfuric acid and the mixture was heated and then cooled, whereby an analytical solution was prepared. The concentration ($K_{Ti}$) of titanium and the concentration ($K_{Fe}$) of iron, which was selected as a reference element, in the analytical solution were each determined with an ICP mass spectrometer. The concentration ratio ($K_{Ti}/K_{Fe}$) was multiplied by the content ($C_{Fe}$) of the reference element (the composition value of iron in Table 4), whereby the solid solution content (sol. $C_{Ti}$) of titanium in the specimen was determined.

Comparative Method

Specimens B shown in Table 5 were used as samples. About 0.5 g of each specimen was electrolyzed at a constant potential in about 300 ml of a 10% AA electrolytic solution (ten volume percent acetylacetone, one mass percent tetramethylammonium chloride, and methanol). After electrolysis was finished, ultrasonic waves were applied to the specimen in the electrolytic solution, whereby precipitates attached to the specimen were intentionally dispersed in the electrolytic solution. About 5 ml of the electrolytic solution was sampled into a beaker while being stirred and was then dried. The residue thereby obtained was dissolved in a mixture of nitric acid, perchloric acid, and sulfuric acid by heating and was then cooled, whereby an analytical solution was prepared. The concentration ($K_{Ti}$) of titanium and the concentration ($K_{Fe}$) of iron, which was selected as a reference element, in this analytical solution were each determined with an ICP mass spectrometer. The concentration ratio ($K_{Ti}/K_{Fe}$) was multiplied by the content ($C_{Fe}$) of the reference element (the composition value of iron in Table 4), whereby the solid solution content (sol. $C_{Ti}$) of titanium in the specimen was determined.

Table 7 summarizes the solid solution content of titanium determined by the inventive method and that by the comparative method. The solid solution content of titanium determined by the inventive method is substantially equal to that by the inventive method described in Example 2. However, the solid solution content of titanium determined by the comparative method is twice or more that by the inventive method described in Example 2. This is because although the sampled electrolytic solution contains the precipitates, the inventive method allows the precipitates to be removed therefrom and therefore gives an accurate dissolved titanium analytical measurement and the comparative method does not allow the precipitates to be removed therefrom and therefore gives a dissolved titanium analytical measurement including the amount of precipitated titanium and dissolved titanium. This shows that the inventive method is an analytical method that gives an accurate dissolved metal analytical measurement even if precipitates are dispersed in an electrolytic solution.

TABLE 7

| | Solid solution content (mass ppm) | | | |
| --- | --- | --- | --- | --- |
| | Inventive method | | Comparative method | |
| Specimens | Measurements | Average | Measurements | Average |
| Specimens B | 850 | 818 | 1966 | 1999 |
| | 797 | | 2050 | |
| | 785 | | 1971 | |
| | 841 | | 2010 | |

What is claimed is:

1. A method for analyzing a metal specimen, comprising:
   an electrolysis step of electrolyzing a metal specimen containing a reference element and a target element in an electrolytic solution;
   a sampling step of sampling a portion of the electrolytic solution;
   an analysis step of analyzing the sampled electrolytic solution;
   a concentration ratio-calculating step of calculating a concentration ratio of the target element to the reference element in the electrolytic solution on the basis of the analysis results; and
   a content-calculating step of calculating the content of the target element existing in a form of a solid solution by multiplying the obtained concentration ratio by the content of the reference element in the metal specimen.

2. The method according to claim 1, wherein the sampling step comprises sampling a portion of the electrolytic solution during electrolysis.

3. The method according to claim 1, wherein the sampling step comprises sampling a portion of the electrolytic solution after electrolysis.

4. The method according to claim 1, wherein the sampling step comprises removing remaining metal specimen from the electrolytic solution after electrolysis and then sampling a portion of the electrolytic solution.

5. The method according to claim 1, wherein the sampling step comprises filtering the electrolytic solution and then sampling a portion of the filtered electrolytic solution.

6. The method according to claim 1, wherein the sampling step comprises sampling the electrolytic solution of 5 ml or less.

7. The method according to claim 1, further comprising the step of dialyzing the sampled electrolytic solution through a semipermeable membrane to remove precipitates and inclusions.

8. The method according to claim 1, wherein the analysis step comprises:
   an aqueous solution-preparing step of adding a chelating agent to the sampled electrolytic solution to prepare an aqueous solution;
   a checking step of checking that the aqueous solution contains no fine particles; and
   an aqueous solution-analyzing step of analyzing the checked aqueous solution.

9. The method according to claim 1, wherein the reference element is an element which forms no precipitate or inclusion.

10. The method according to claim 1, wherein
    the metal specimen is steel; and
    the reference element is iron.

11. The method according to claim 1, wherein
    the metal specimen is stainless steel; and
    the reference element is chromium or nickel.

12. The method according to claim 1, wherein
    the metal specimen is a copper alloy; and
    the reference element is copper.

13. The method according to claim 1, wherein the analysis step comprises mixing the sampled electrolytic solution with an aqueous solution of a chelating agent to convert the reference element and the target element into water-soluble chelates, and then performing analysis.

14. The method according to claim 13, wherein the chelating agent aqueous solution is an aqueous solution of ethylenediaminetetraacetic acid.

15. A method for analyzing a metal specimen, comprising:
    an electrolysis step of electrolyzing a metal specimen containing a reference element and a target element in an electrolytic solution;
    a sampling step of sampling a portion of the electrolytic solution;
    an analysis step of analyzing the sampled electrolytic solution which comprises:
       an aqueous solution-preparing step of adding a chelating agent to the sampled electrolytic solution to prepare an aqueous solution;
       a checking step of checking that the aqueous solution contains no fine particles by introducing the aqueous solution into a high-sensitivity analyzer and then checking the aqueous solution on the basis of the stability of the intensity of a signal obtained by time-resolved photometry; and
       an aqueous solution-analyzing step of analyzing the checked aqueous solution;
    a concentration ratio-calculating step of calculating a concentration ratio of the target element to the reference element in the electrolytic solution on the basis of the analysis results; and
    a content-calculating step of calculating the content of the target element existing in a form of a solid solution by multiplying the obtained concentration ratio by the content of the reference element in the metal specimen.

* * * * *